United States Patent [19]
Nardi et al.

[11] Patent Number: 4,675,319
[45] Date of Patent: Jun. 23, 1987

[54] ANTIANAPHYLACTIC AND ANTIBRONCHOSPASTIC PIPERAZINYL-(N-SUBSTITUTED PHENYL)CARBOXAMIDES, COMPOSITIONS AND USE

[75] Inventors: Dante Nardi; Amedeo Leonardi; Gianni Motta; Pietro Cazzulani, all of Milan, Italy

[73] Assignee: Recordati S. A. Chemical and Pharmaceutical Company, Chiasso, Switzerland

[21] Appl. No.: 871,858

[22] Filed: Jun. 9, 1986

[30] Foreign Application Priority Data

Jun. 20, 1985 [IT] Italy ................................ 21225 A/85

[51] Int. Cl.$^4$ ................. A61K 31/495; A61K 31/535; C07D 295/14; C07D 413/12
[52] U.S. Cl. .................................... 514/234; 514/252; 514/255; 544/82; 544/121; 544/357; 544/360; 544/372; 544/374; 544/396
[58] Field of Search ................. 544/82, 121, 357, 360, 544/372, 374, 396; 514/234, 252, 255

[56] References Cited
U.S. PATENT DOCUMENTS
3,244,718  4/1966  Biel .................................... 544/396

Primary Examiner—Robert W. Ramsuer
Attorney, Agent, or Firm—Burns, Doane, Swecker & Mathis

[57] ABSTRACT

Novel piperazine derivatives having the general formula:

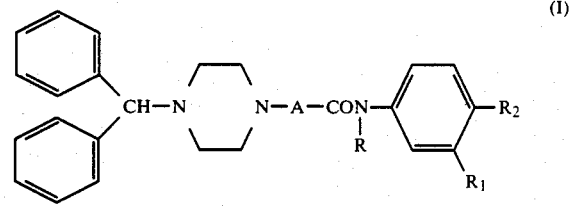

wherein R is hydrogen or lower alkyl, A is straight or branched chain lower alkyl, and $R_1$ and $R_2$ are each hydrogen, amino, alkylamino, dialkylamino, mono- or di(hydroxyalkyl)amino, morpholino, pyrrolidino, piperidino, N-alkylpiperazino, 1,3-dithiolan-2-ylidenamino, or N-alkylureido, with the proviso that at least one of $R_1$ and $R_2$ is other than hydrogen, or the isomeric mixtures, individual enantiomers or pharmaceutically acceptable acid addition salts thereof, are therapeutically useful antianaphylactic and antibronchospastic agents.

34 Claims, No Drawings

ANTIANAPHYLACTIC AND ANTIBRONCHOSPASTIC PIPERAZINYL-(N-SUBSTITUTED PHENYL)CARBOXAMIDES, COMPOSITIONS AND USE

BACKGROUND OF THE INVENTION

1. Field of the Invention

The present invention relates to novel antianaphylactic and antibronchospastic piperazine derivatives, to isomeric mixtures, individual enantiomers and pharmaceutically acceptable acid addition salts thereof, to a process for their preparation and to pharmaceutical compositions comprising same with a pharmaceutically acceptable carrier or diluent thereof.

2. Description of the Prior Art

In U.S. Pat. No. 3,244,718, certain carboxamido piperazine derivatives of benzhydryl type are described which are useful as antihistaminic, antiserotonin and antiallergic agents, and while it is reported that the phenyl ring attached via the carboxamidoethyl radical to the piperazine moiety may be variously substituted, in the preparative examples only one specific instance is noted wherein said ring is substituted, by a trifluoromethyl group, but here the benzhydryl group is conspicuously absent.

SUMMARY OF THE INVENTION

Accordingly, a major object of the present invention is the provision of a novel class of benzhydryl piperazine derivatives comprising a critically substituted phenyl moiety attached to the piperazine nucleus via a carboxamidoalkyl bridge, which critical substituents impart to said novel piperazine derivatives a high degree of antianaphylactic and antibronchospastic activity.

Briefly, the novel piperazino compounds featured by the present invention have the general formula:

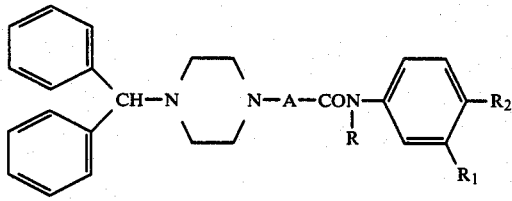

(I)

wherein R is hydrogen or lower alkyl, A is straight or branched chain lower alkyl, and $R_1$ and $R_2$ are each hydrogen, amino, alkylamino, dialkylamino, mono- or di(hydroxyalkyl)amino, morpholino, pyrrolidino, piperidino, N-alkylpiperazino, 1,3-dithiolan-2-ylidenamino, or N-alkylureido, with the proviso that at least one of $R_1$ and $R_2$ is other than hydrogen; as well as the isomeric mixtures, individual enantiomers and pharmaceutically acceptable acid addition salts thereof.

DETAILED DESCRIPTION OF THE PREFERRED EMBODIMENTS OF THE INVENTION

More particularly according to the present invention, by the terms "lower alkyl" and "alkyl" are intended a straight or branched alkyl chain containing from 1 to 5 carbon atoms, such as methyl, ethyl, propyl, isopropyl, n-butyl, iso-butyl, t-butyl, sec-butyl and the like. Exemplary of the pharmaceutically acceptable acid addition salts, representative are the addition salts of both organic and inorganic acids, such as, for example, hydrochloric, sulfuric, sulfamic, tartaric, hydrobromic acid, hydrogen iodide, glycolic, citric, malic, phosphoric, succinic, acetic, ascorbic acid and the like. These may be prepared by simple addition of one or more acid equivalents to the free base.

The intermediates and final products according to the present invention are advantageously prepared by known procedures. Thus, the starting compound employed in the following examples, namely N-benzhydrylpiperazine (II), has been described in several patents and in the open literature, or it can facilely be prepared according to known procedures [see, for example: K. E. Hamlin et al., *J. Am. Chem. Soc.*, 71, 2731 (1949); or British Pat. Nos. 752,331 and 752,332 (July 11, 1956)].

To prepare the novel compounds of this invention, the starting material (II) is reacted with an acryloylanilide derivative of the formula:

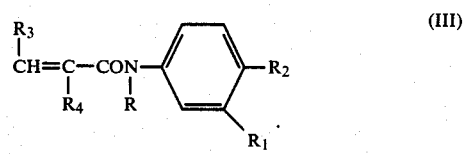

(III)

wherein $R_3$ and $R_4$ are hydrogen or lower alkyl and R, $R_1$ and $R_2$ are as defined above, or with a compound of the formula:

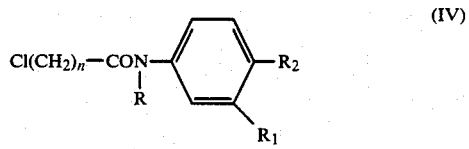

(IV)

wherein n is an integer ranging from 1 to 5.

In such preparation, the reagents are dissolved, in equimolar amounts, in a suitable solvent, for example, dimethylformamide, toluene, xylene and the like, and heated for several hours at a temperature ranging from 50° to 100° C. When dimethylsulfoxide is employed as the solvent, the reaction temperature can be lowered considerably, allowing operation at from 10° to 40° C.

Upon completion of the reaction, the desired intermediate thus obtained is collected, for example by filtration or evaporation of the solvent, and eventually purified by silica gel chromatography and/or crystallization from a suitable solvent. when desired, the compound may ultimately be transformed into a pharmaceutically acceptable acid addition salt thereof.

The novel compounds of the present invention are characterized by high antianaphylactic and antibronchospastic activity and by a low toxicity. The LD$_{50}$ of the novel piperazine derivatives has been determined in the mouse, both ip and per os, following the method described by C. S. Weil, *Biometrics*, 8, 249 (1952). The results obtained are reported in the Table which follows. In order to evaluate the antianaphylactic activity of said novel compounds, the method of Goose and Blair was followed, in which passive cutaneous anaphylaxis (PCA) was induced in the rat with homologous antibodies [*Immunology*, 16, 749, (1969)].

Female albino rate were immunized intramuscularly with egg albumin and intraperitoneally with Haemophylus pertussis vaccine. Twelve days after treatment, the animals were bled and sera thus obtained were injected intradermally into another group of rats. Twenty-four hours later, the animals were challenged with an i.v. solution of ovoalbumin and Evans blue dye, and sacrificed after 30 minutes. The test drugs were given by different routes of administration and at different times before the challenge. Inhibition of spots areas ($ED_{50}$) was determined. The results obtained are also reported in the Table which follows.

The antibronchospastic activity was determined according to the method of Konzett and Roessler, *Arch., Exp. Path. Pharmakol.*, 195, 71 (1940), entailing the inhibition of bronchospasm induced in anaesthesized guinea pig by histamine and acetylcholine. For this purpose, the bronchospasms were induced by administering intravenously to the animals 0.5-25 µg/kg of hystamine or 2.5-10 µg/kg of acetylcholine. Inhibition ($ED_{50}$) was determined one minute after injection of the drug under test.

Inhibition of passive lung anaphylaxis (PLA) was studied in a model of antigen induced bronchoconstriction in sensitized rat, according to the method described by Greenberg et al, *Can. J. Physiol. Pharmacol.*, 57, 48 (1979). Female albino rate were passively sensitized by intravenous injection of homologous anti-egg albumin serum. Twenty-four hours later the rats were anaesthetized with pentobarbital (35 mg/kg i.p.) and spontaneous respiration was arrested by administration of tubocurarine (0.75 mg/kg i.v.).

Bronchocostriction was induced by egg albumin intravenously administered and measured by the Konzett and Roessler method *Arch. Exp. Path. Pharmakol.*, 195, 71, (1940). The compounds were injected intravenously one minute before antigen challenge. The inhibitory effect ($ED_{50}$) was evaluated 5 and 10 minutes after i.v. administration of the drugs under test.

The $TXA_2$ inhibition was evaluated according to the method of Berti et al *Brit. J. Pharmacol.*, 68, 467 (1980). Lungs from female or male guinea-pigs were perfused through the pulmonary artery with Krebs bicarbonate (5 ml/min, 37° C.). The pulmonary outflow superfused strips of rabbit mesenteric artery and rabbit aorta in cascade, in order to monitor $TXA_2$ activity. These tissues were superfused with a mixture of receptor antagonist and indomethacin to release their selectivity and sensitivity. Lungs were challenged with a single injection of bradykinin (0.25-0.5 µg) which is known to increase generation of $TXA_2$ from the pulmonary tissue. The novel compounds of the invention were perfused at different concentrations through the lungs 30 and 60 minutes before agonists.

In the Table which follows, the results obtained utilizing the above tests are reported. The $LD_{50}$ and the $DE_{50}$ in the PCA test are expressed in mM/kg. The $DE_{50}$ for the antibronchospastic activity (BSP) is expressed in µm/kg i.v. (bronchospasm induced by histamine (H) and acetylcholine (A)). In the $TXA_2$ test, (C) is the concentration in µg/ml, whereas (I%) denotes the maximal inhibition percentage. In the PLA test, the $DE_{50}$ is expressed in µM/kg i.v. (evaluated 5 and 10 minutes after administration).

TABLE

| Compound No. | $LD_{50}$ ip | $LD_{50}$ os | PCA, $ED_{50}$ | BSP, $ED_{50}$ H | BSP, $ED_{50}$ A | $TXA_2$ C | $TXA_2$ I% | PLA, $ED_{50}$ 5' | PLA, $ED_{50}$ 10' |
|---|---|---|---|---|---|---|---|---|---|
| (1) | 0.24 | 0.58 | 0.013 | 0.25 | | | | | |
| (2) | 0.26 | 0.34 | >0.069 | | | | | | |
| (3) | | >7 | 0.025 | 1.10 | 0.8 | 5 | 59 | 0.02 | 0.02 |
| (4) | | 5 | 0.008 | 0.21 | 0.4 | 10 | 47 | 0.04 | 0.08 |
| (5) | | 7.2 | 0.028 | 0.23 | | | | | |
| (6) | >2.33 | >7 | 0.010 | 0.12 | 0.4 | 10 | 0.8 | 0.65 | 0.69 |
| (7) | 1.75 | >5.90 | 0.073 | | | | | | |
| (8) | 0.23 | 0.43 | 0.010 | 1.10 | >3 | | | 0.84 | 0.84 |

In order to further illustrate the present invention and the advantages thereof, the following specific examples are given, it being understood that same are intended only as illustrative and in nowise limitative.

EXAMPLES

Preparation of the Intermediates (a) A mixture of 12.6 g of N,N-dimethyl-m-phenylendiamine dihydrochloride, 4.8 g of sodium hydroxide and 60 ml of acetic acid was stirred for 5 hours at 20°-25° C. At the same temperature, 5.76 ml of acryloylchloride were added dropwise. The suspension was stirred and, one hour later, a solution of 36.3 g of sodium acetate trihydrate in 90 ml of water was slowly added, also dropwise. The solution was allowed to stand for 24 hours, then it was diluted with 150 ml of water and alkalinized with concentrated sodium hydroxide. The oily precipitate was extracted with ethyl acetate and the organic phase dried on anhydrous sodium sulfate. The residue obtained by evaporation of the solvent was purified by silica gel chromatography, eluting with ethyl acetate. The fractions unitary at TLC were collected and the solvent was evaporated off. The residue was crystallized from ethyl acetate/petroleum ether to give 5.8 g of 3'-dimethylaminoacryoylanilide, melting at 101°-103° C.

Utilizing the above procedure, the following intermediates were also prepared:
4'-diethylaminoacryloylanilide, mp 122° C.;
4'-dimethylaminoacryloylanilide, mp 143°-144° C.;
4'-(1-piperidinyl)acryloylanilide, mp 147°-148° C.;
4'-(1-morpholinyl)acryloylanilide, mp 220°-222° C.;
4'-dimethylamino-N-methylacryloylanilide, mp 59°-62° C.;
4'-(4-methyl-1-piperazinyl)acryloylanilide, mp 191°-193° C.;
4'-(1-imidazolyl)acryloylanilide, mp 181°-183° C.;
4'-bis-(2-hydroxyethyl)aminoacryloylanilide, mp 142.5° C.;
3'-nitro-N-methylacryloylanilide, mp 68° C.

Again utilizing the above procedure, but employing a suitably substituted acid chloride instead of acryloylchloride, the following compounds also were prepared:
4'-dimethylaminocrotonylanilide, mp 173°-147° C.;
4'-dimethylaminomethacryloylanilide, mp 127°-130° C.

(b) A mixture of 21 g of N-N-dimethyl-p-phenylendiamine dihydrochloride, 41.8 ml of $Et_3N$ and 80 ml of chloroform was stirred at 20°-23° C. for 30 minutes. At the same temperature and within twenty minutes, a solution of 11.3 mol of 4-chlorobutyrylchloride in 20 ml of chloroform was added dropwise. The mixture was stirred for two hours and then diluted and shaken with about 300 ml of water. The organic phase was separated off, dried on calcium chloride/anhydrous sodium sulfate, filtered and evaporated to dryness. The residue thus obtained was purified by silica gel chromatography, employing ethyl acetate as eluent. The fractions unitary to TLC were collected, the solvent was evaporated off under vacuum and the residue crystallized from carbon tetrachloride to give 14.8 g of 4'-dimethylamino-4-chlorobutyrylanilide melting at 119° C.

(c) Operating as described in the following Example 1, but employing m-nitroacryloylanilide instead of 4'-diethylaminoacryloylanilide, the intermediate 3-(4-benzhydryl-1-piperazinyl)-N, 3-nitrophenylpropionamide was prepared, melting at 158°–159° C.

In the same manner, but employing p-nitroacryloylanilide, the N,4-nitrophenylpropionamide derivative was prepared, melting at 177°–179° C.

EXAMPLE 1

Preparation of
3-(4-benzhydryl-1-piperazinyl)-N,4-diethylaminophenylpropionamide (9)

A mixture comprising 8.82 g of N-benzhydrylpiperazine, 7.64 g of 4'-diethylaminoacryloylanilide and 70 ml of toluene was refluxed for 6 hours under stirring. Upon completion of the reaction, the solvent was evaporated under vacuum and the crude product was chromatographed on a silica gel column using ethyl acetate as eluent. The fractions containing the desired product were collected, the solvent was evaporated off and the crude product was crystallized from ethyl acetate and petroleum ether to give 4.8 g of the title compound (9) melting at 112°–114° C.

Repeating the above procedure, but employing a suitably substituted acryloylanilide instead of 4'-diethylaminoacryloylanilide, the following compounds were prepared:

3-(4-benzhydryl-1-piperazinyl)-N,3-dimethylaminoophenylpropionamide trihydrochloride hemihydrate (2), mp 211°–213° C.;
3-(4-benzhydryl-1-piperazinyl)-N,4-dimethylaminophenylpropionamide (3), mp 155°–157° C.;
3-(4-benzhydryl-1-piperazinyl)-N,4-(1-morpholino)-phenylpropionamide (10), mp 157°–159° C.;
3-(4-benzhydryl-1-piperazinyl)-N,4-(1-piperidino)-phenylpropionamide (11), mp 135°–137° C.;
3-(4-benzhydryl-1-piperazinyl)-N-methyl-N,4-dimethylaminophenylpropionamide (12), mp 139°–141° C.;
3-(4-benzhydryl-1-piperazinyl)-N-(4-bis-(2-hydroxyethyl)aminophenyl)propionamide (13), mp 150°–152° C.

Repeating the above procedure, but employing 4'-dimethylaminocrotonylanilide instead of 4'-diethylaminoacryloylanilide, and using xylene instead of toluene at the solvent, 3-(4-benzhydryl-1-piperazinyl)-N,4-dimethylaminophenylbutyramide (14), mp 148° C., was prepared.

EXAMPLE 2

Preparation of
3-(4-benzhydryl-1-piperazinyl)-N,4-(4-methyl-1-piperazinyl)phenylpropionamide (15)

A mixture comprising 2.45 g of 4'-(4-methyl-1-piperazinyl)acryloylanilide, 2.52 g of N-benzhydrylpiperazine and 20 ml of DMSO was stirred for 6 hours at 80° C. Upon completion of the reaction the cooled solution was poured into about 200 ml of water and the mixture was extracted with ethyl acetate. The organic phase was separated, washed with water, dried on anhydrous sodium sulfate, filtered and evaporated to dryness. The residue thus obtained was purified on a silica gel column, eluting with a 5% solution of acetic acid in water. The fractions containing the desired product were collected and alkalinized by adding 30% sodium hydroxide. The precipitate was collected by filtration, dried and crystallized from ethyl acetate/petroleum ether to give 2 g of the title compound (15) melting at 158°–156° C.

Repeating the above procedure, but employing 4'-(1-imidazolyl)acryloylanilide instead of 4'-(4-methyl-1-piperazinyl)acryloylanilide, 3-(4-benzhydryl-1-piperazinyl)-N, 4-(1-imidazolyl)phenylpropionamide (16), mp 103°–105° C. (dec), was prepared.

EXAMPLE 3

Preparation of
3-(4-benzhydryl-1-piperazinyl)-N,3-aminophenylpropionamide (4)

A mixture comprising 12 g of zinc powder, 4.38 g of calcium chloride dihydrate in 12 ml of water and 39 ml of ethanol was stirred and heated for one hour at 80° C. Added thereto were 13.32 g. of 3-(4-benzhydryl-1-piperazinyl)-N,3-nitrophenylpropionamide, prepared as described in Example 1, and the mixture was then stirred for an additional 5 hours at the same temperature. Upon completion of the reaction the insoluble fraction was filtered off and the solvent was evaporated under vacuum. The residue thus obtained was purified by column chromatography (silica gel) with chloroform/methanol (95:5) as eluent. Fractions unitary at TLC were collected, the solvent was evaporated under vacuum and the residue crystallized from ethanol (or ethyl acetate) and petroleum ether to give 5.9 g of the title compound (4) melting at 151°–154° C.

Repeating the above procedure, but using 3-(4-benzhydryl-1-piperazinyl)-N,4-nitrophenylpropionamide as the starting material, the corresponding 4-aminoderivative (5) melting at 170°–172° C. was prepared.

EXAMPLE 4

Preparation of
3-(4-benzhydryl-1-piperazinyl)-N,4-methylureidophenylpropionamide (7)

A mixture comprising 62 g of 3-(4-benzhydryl-1-piperazinyl)-N, 4-aminophenylpropionamide, prepared as described in the previous Example, 0.87 g of methylisocyanate and 30 ml of toluene was heated under stirring for 3 hours at 100° C. Upon completion of the reaction the mixture was cooled and the solid thus precipitated was collected by filtration and crystallized from acetone to give 6.5 g of the title compound (7) melting at 205°–207° C. The hydrochloride, obtained by adding to the base hydrochloric acid in ethanol, melted at 160°–163° C.

EXAMPLE 5

Preparation of 4-(4-benzhydryl-1-piperazinyl)-N,4-dimethylaminophenylbutyramide (8)

A mixture of 10.83 g of 4'-dimethylamino-4-chlorobutyrylanilide, 22.68 g of N-benzhydrylpiperazine, 7.38 g of potassium iodide and 180 ml of DMSO was stirred for 7 days at 18°–23° C. Upon completion of the reaction, the mixture was poured into about 1.8 l of 0.25 N sodium hydroxide and extracted with ethyl acetate. The organic phase thus separated was dried on anhydrous sodium sulfate, filtered and evaporated to dryness. The residue thus obtained was purified on a silica gel column, eluting with ethyl acetate. The fractions containing the desired product were collected, the solvent was evaporated off and the residue was dissolved in ethanol and added with hydrochloric acid in ethanol and subsequently with ethyl ether until turbid. The hydrochloride thus crystallized was collected by filtration and recrystallized from ethanol or methanol to give 8 g of the title compound (8) melting at 192°–195° C. (dec).

EXAMPLE 6

Preparation of 3-(4-benzhydryl-1-piperazinyl)-N,3-methylaminophenylpropionamide (1)

A mixture comprising 15.5 g of the compound (4) described in Example 3, 4.4 g of succinimide, 3.37 g of 37% formaldehyde solution and 92 ml of ethanol was refluxed under stirring for 10 hours. After cooling at 20°–25° C. the solvent was evaporated off under vacuum and the residue was purified on a silica gel column using ethyl ether/methanol (9:1) as eluent. From the last fractions, which were collected and evaporated to dryness, 10.5 g of 3-(4-benzhydryl-1-piperazinyl)-N,3-(succinimidoethyl)aminophenylpropionamide, as a dark oil, were obtained, which was then employed as such for the next reaction. To 10.5 g of the product obtained as described above, dissolved in 30 ml of DMSO at 50°–60° C., 0.88 g of sodium borohydride were added dropwise. When the addition was complete, the solution thus obtained was heated under stirring for 30 minutes at 100° C. and subsequently cooled at 20°–25° C., poured into about 400 ml of water, acidified with dilute hydrochloric acid and, after standing overnight, alkalinized with dilute sodium hydroxide.

The precipitate thus obtained was collected by filtration and purified by silica gel chromatography, employing ethyl acetate as eluent. The fractions unitary at TLC were collected, the solvent was evaporated off, the residue dissolved in ethanol and the solution acidified with hydrochloric acid in ethanol. A solid product crystallized that was collected by filtration and recrystallized from ethanol to give 4.5 g of the title compound (1) as the trihydrochloride hemihydrate, melting at 203°–204° C.

Repeating the above procedure, but employing 3-(4-benzhydryl-1-piperazinyl)-N,4-aminophenylpropionamide (5) instead of the 3-aminophenyl derivative (4), 3-(4-benzhydryl-1-piperazinyl)-N, 4-methylaminophenylpropionamide (17), melting at 140°–141° C., was prepared.

EXAMPLE 7

Preparation of 3-(4-benzhydryl-1-piperazinyl)-N,3-aminophenvl-N-methylpropionamide (6)

A mixture of 19 g of 3'-nitro-N-methyacryloylanilide, 23 g of N-benzhydrylpiperazine and 185 ml of toluene was refluxed under stirring for 3 hours. Upon completion of the reaction, the solvent was evaporated off under vacuum and the residue was dissolved in ethyl acetate and filtered with silica gel in order to eliminate th N-benzhydrylpiperazine still present.

The filtrate was then evaporated to dryness, the residue dissolved in ethyl ether and then filtered. By adding hydrochloric acid in ethanol, 3-(4-benzhydryl-1-piperazinyl)-N-methyl-N, 3-nitrophenylpropionamide hydrochloride hemihydrate was prepared, which was then dissolved in ethanol/ethyl acetate and crystallized until a constant melting point was reached (180°–182° C.), giving a yield of 17.2 g.

A mixture comprising 15.6 g of the compound described above, 35.5 g of stannous chloride dihydrate and 95 ml of ethanol was heated under stirring for 3 hours at 70° C. in nitrogen atmosphere. Upon completion of the reaction, the mixture was cooled at 20°–25° C., the solvent was evaporated off under vacuum and the residue was treated with about 400 ml of water. After alkalinization with dilute sodium hydroxide, extraction with ethyl acetate was carried out. The solvent was evaporated, the residue was milled with about 150 ml of water and the solid thus obtained collected by filtration, air dried and crystallized from ethanol or isopropyl acetate to give 10.2 g of the title compound (6) melting at 144°–146° C.

EXAMPLE 8

Preparation of 3-(4-benzhydryl-1-piperazinyl)-N-3-(1,3-dithiolan-2-yliden)aminophenylpropionamide (18)

To 1.11 g of (1,3-dithiolan-2-yliden)methylsulfonium iodide (prepared as described by R. Mayer and K. Schafer, J. Prakt. Chem., 26, 279 (1964)), dissolved in 3.3 ml of DMF at 20°–23° C., were added dropwise within 20 minutes, 1.66 g of the compound described in Example (c) dissolved in 13.3 ml of DMF.

The mixture was heated under stirring for 13 hours at 50° C., then it was cooled and poured into 100 ml of 0.2 N sodium hydroxide. The crude product was collected by filtration and purified by chromatography on a silica gel column employing chloroform/methanol (95:5) as eluent. The fractions unitary at TLC were collected, the solvent was evaporated off and the resulting residue was crystallized from $CH_3CN$ to give 0.3 g of the title compound (18) melting at 219°–220° C.

EXAMPLE 9

Preparation of 2-methyl-3-(4-benzhydryl-1-piperazinyl)-N,4dimethylaminophenylpropionamide (19)

A mixture of 12.6 g of 4'-dimethylaminomethacryloylanilide, 16.63 g of N-benzhydrylpiperazine and 43 ml of N,N-dimethylacetamide was stirred and refluxed for 3 hours. Upon completion of the reaction, the mixture was cooled, poured into about 600 ml of water, extracted with ethyl ether and washed with water. The phases were separated and the organic layer was dried on anhydrous sodium sulfate. The solvent was evaporated and the residue thus obtained was filtered off and purified on a silica gel column employing a 3:2 ethyl acetate/petroleum ether mixture and then only ethyl acetate as eluent. The fractions unitary at TLC were collected, the solvent was evaporated under vacuum, the residue was dissolved in ethanol and acidified with hydrochloric acid in ethanol. The title compound (19) was collected by filtration as the trihydrochloride and crystallized from ethanol and ethyl ether until mp of 228°–232° C. (yield 9.5 g) was obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the general formula:

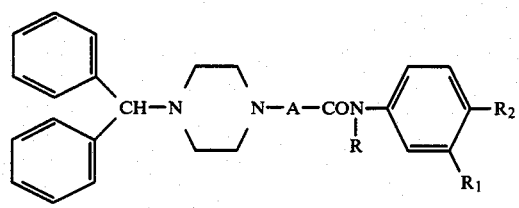

(I)

wherein R is hydrogen or lower alkyl, A is straight or branched chain lower alkyl and $R_1$ and $R_2$ are each hydrogen, amino, alkylamino, dialkylamino, mono- or di(hydroxyalkyl)amino, morpholino, pyrrolidino, piperidino, N-alkylpiperazino, 1,3-dithiolan-2-ylidenamino, or N-alkylureido, with the proviso that at least one of $R_1$ and $R_2$ is other than hydrogen, or an isomeric mixture, individual enantiomer or pharmaceutically acceptable acid addition salt thereof.

2. A compound as defined by claim 1, wherein at least one of $R_1$ and $R_2$ is amino.

3. A compound as defined by claim 1, wherein at least one of $R_1$ and $R_2$ is alkylamino.

4. A compound as defined by claim 1, wherein at least one of $R_1$ and $R_2$ is dialkylamino.

5. A compound as defined by claim 1, wherein at least one of $R_1$ and $R_2$ is mono(hydroxyalkyl)amino.

6. A compound as defined by claim 1, wherein at least one of $R_1$ and $R_2$ is di(hydroxylalkyl)amino.

7. A compound as defined by claim 1, wherein at least one of $R_1$ and $R_2$ is morpholino.

8. A compound as defined by claim 1, wherein at least one of $R_1$ and $R_2$ is pyrrolidino.

9. A compound as defined by claim 1, wherein at least one of $R_1$ and $R_2$ is piperidino.

10. A compound as defined by claim 1, wherein at least one of $R_1$ and $R_2$ is N-alkylpiperazino.

11. A compound as defined by claim 1, wherein at least one of $R_1$ and $R_2$ is 1,3-dithiolan-2-ylidenamino.

12. A compound as defined by claim 1, wherein at least one of $R_1$ and $R_2$ is N-alkylureido.

13. A compound as defined by claim 1, the same being 3-(4-benzhydryl-1-piperazinyl)-N,4-diethylaminophenylpropionamide.

14. A compound as defined by claim 1, the same being 3-(4-benzhydryl-1-piperazinyl)-N,4-(1-morpholino)-phenylpropionamide.

15. A compound as defined by claim 1, the same being 3-(4-benzhydryl-1-piperazinyl)-N,4-(1-piperidino)-phenylpropionamide.

16. A compound as defined by claim 1, the same being 3-(4-benzhydryl-1-piperazinyl)-N,3-dimethylaminophenylpropionamide.

17. A compound as defined by claim 1, the same being 3-(4-benzhydryl-1-piperazinyl)-N,4-dimethylaminophenylpropionamide.

18. A compound as defined by claim 1, the same being 3-(4-benzhydryl-1-piperazinyl)-N-methyl-N,4-dimethylaminophenylpropionamide.

19. A compound as defined by claim 1, the same being 3-(4-benzhydryl-1-piperazinyl)-N-(4,bis-(2-hydroxyethyl)aminophenyl)propionamide.

20. A compound as defined by claim 1, the same being 3-(4-benzhydryl-1-piperazinyl)-N,4-dimethylaminophenylbutyramide.

21. A compound as defined by claim 1, the same being 3-(4-benzhydryl-1-piperazinyl)-N,4-(4-methyl-1-piperazinyl)phenylpropionamide.

22. A compound as defined by claim 1, the same being 3-(4-benzhydryl-1-piperazinyl)-N,4-(1-imidazolyl)-phenylpropionamide.

23. A compound as defined by claim 1, the same being 3-(4-benzhydryl-1-piperazinyl)-N,3-aminophenylpropionamide.

24. A compound as defined by claim 1, the same being 3-(4-benzhydryl-1-piperazinyl)-N,4-aminophenylpropionamide.

25. A compound as defined by claim 1, the same being 3-(4-benzhydryl-1-piperazinyl)-N,4-methylureidophenylpropionamide.

26. A compound as defined by claim 1, the same being 3-(4-benzhydryl-1-piperazinyl)-N,4-dimethylaminophenylbutyramide.

27. A compound as defined by claim 1, the same being 3-(4-benzhydryl-1-piperazinyl)-N,3-methylaminophenylpropionamide.

28. A compound as defined by claim 1, the same being 3-(4-benzhydryl-1-piperazinyl)-N,4-methylaminophenylpropionamide.

29. A compound as defined by claim 1, the same being 3-(4-benzhydryl-1-piperazinyl)-N,3-aminophenyl-N-methylpropionamide.

30. A compound as defined by claim 1, the same being 3-(4-benzhydryl-1-piperazinyl)-N,3-(1,2-dithiolan-2-yliden)aminophenylpropionamide.

31. A compound as defined by claim 1, the same being 2-methyl-3-(4-benzhydryl-1-piperazinyl)-N,4-dimethylaminophenylpropionamide.

32. A composition of matter comprising a compound as defined by claim 1, or isomeric mixture, individual enantiomer or acid addition salt thereof, and a pharmaceutically acceptable carrier or diluent therefor.

33. A method for eliciting an antianaphylactic or antibronchospastic response in a mammalian organism in need of such treatment, comprising administering thereto a therapeutically effective amount of a compound as defined by claim 1, or isomeric mixture, individual enantiomer or pharmaceutically acceptable acid addition salt thereof.

34. A method for eliciting an antianaphylactic or antibronchospastic response in a mammalian organism in need of such treatment, comprising administering thereto a therapeutically effective amount of the composition of matter as defined by claim 32.

* * * * *